(12) United States Patent
Ukai et al.

(10) Patent No.: US 11,730,880 B2
(45) Date of Patent: Aug. 22, 2023

(54) PREFILLED SYRINGE STORAGE TRAY AND PACKAGE USING THE SAME

(71) Applicant: TERUMO KABUSHIKI KAISHA, Tokyo (JP)

(72) Inventors: Atsushi Ukai, Yamanashi (JP); Yosuke Kurihara, Yamanashi (JP); Junichi Ogawa, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 129 days.

(21) Appl. No.: 17/487,316

(22) Filed: Sep. 28, 2021

(65) Prior Publication Data

US 2022/0008645 A1    Jan. 13, 2022

Related U.S. Application Data

(63) Continuation of application No. PCT/JP2020/006311, filed on Feb. 18, 2020.

(30) Foreign Application Priority Data

Mar. 28, 2019    (JP) ................................ 2019-063869

(51) Int. Cl.
*A61M 5/00* (2006.01)
*A61M 5/31* (2006.01)
(Continued)

(52) U.S. Cl.
CPC .......... *A61M 5/002* (2013.01); *A61M 5/3129* (2013.01); *A61M 5/31515* (2013.01);
(Continued)

(58) Field of Classification Search
CPC ............. A61M 5/002; A61M 5/3129; A61M 5/31515; A61M 2005/3131; B65D 5/38; B65D 5/5038; B65D 77/0433
(Continued)

(56) References Cited

U.S. PATENT DOCUMENTS 6,012,595 A    1/2000    Thilly
6,267,256 B1    7/2001    Thilly
(Continued)

FOREIGN PATENT DOCUMENTS

JP    H08504628 A    5/1996
JP    2010110339 A    5/2010
(Continued)

OTHER PUBLICATIONS

International Search Report (PCT/ISA/210) with translation and Written Opinion (PCT/ISA/237) dated Apr. 21, 2020, by the Japanese Patent Office as the International Searching Authority for International Application No. PCT/JP2020/006311. (8 pages).
(Continued)

*Primary Examiner* — Jacob K Ackun

(74) *Attorney, Agent, or Firm* — Buchanan Ingersoll & Rooney PC

(57) ABSTRACT

When at least a part of a shaft portion of a plunger is stored in a proximal end side storage portion of a storage tray, the proximal end side storage portion supports a syringe body and the plunger in a state in which the syringe body and the plunger cannot approach each other since a first contact portion comes into contact with a proximal end surface of a body flange and a second contact portion comes into contact with a distal end surface of a pressing operation portion, and the part of the shaft portion of the plunger is prevented from separating since protruding pieces come into contact with the part of the shaft portion of the plunger.

20 Claims, 9 Drawing Sheets

(51) Int. Cl.
  *A61M 5/315* (2006.01)
  *B65D 5/38* (2006.01)
  *B65D 5/50* (2006.01)
  *B65D 77/04* (2006.01)

(52) U.S. Cl.
  CPC .............. *B65D 5/38* (2013.01); *B65D 5/5038* (2013.01); *B65D 77/0433* (2013.01); *A61M 2005/3131* (2013.01)

(58) Field of Classification Search
  USPC .................................................. 206/366, 564
  See application file for complete search history.

(56) References Cited

U.S. PATENT DOCUMENTS

| | | | | |
|---|---|---|---|---|
| 2004/0238391 A1* | 12/2004 | Pond | ....................... | A61C 19/02 206/369 |
| 2010/0012537 A1 | 1/2010 | Farrar et al. | | |
| 2013/0062245 A1* | 3/2013 | Folchini | ................ | A61M 5/002 493/162 |
| 2015/0129442 A1 | 5/2015 | Head et al. | | |
| 2017/0367780 A1* | 12/2017 | Van Der Raad-Meijer | ................. | B65D 75/366 |
| 2018/0361056 A1* | 12/2018 | Horlock | ................ | A61M 5/002 |
| 2019/0184090 A1 | 6/2019 | Ogawa et al. | | |
| 2020/0023117 A1* | 1/2020 | Maruyama | ............. | B65D 81/05 |

FOREIGN PATENT DOCUMENTS

| | | |
|---|---|---|
| JP | 2011528602 A | 11/2011 |
| WO | 2013/176703 A1 | 11/2013 |
| WO | 2018/038077 A1 | 3/2018 |

OTHER PUBLICATIONS

The extended European Search Report dated Apr. 8, 2022, by the European Patent Office in corresponding European Patent Application No. 20777311.0-1122. (25 pages).

* cited by examiner

PREFILLED SYRINGE STORAGE TRAY AND PACKAGE USING THE SAME

CROSS-REFERENCES TO RELATED APPLICATIONS

This application is a continuation of International Application No. PCT/JP2020/006311 filed on Feb. 18, 2020, which claims priority to Japanese Patent Application No. 2019-063869 filed on Mar. 28, 2019, the entire content of both of which is incorporated herein by reference.

FIELD OF THE DISCLOSURE

The present disclosure generally relates to a prefilled syringe storage tray and a package using the same.

BACKGROUND DISCUSSION

In the related art, a prefilled syringe filled with a medicine or the like in advance is known. Such a prefilled syringe includes a syringe body filled with a medicine, a sealing member for sealing a distal end portion of the syringe body, a gasket slidably housed in the syringe body, and a plunger for moving a gasket.

Furthermore, various kinds of packaging materials can be used as a packaging material for storing a plurality of products. For the packaging material for storing a medical tool such as the prefilled syringe described above, a more advanced function than the packaging material for storing a general product is required. As the packaging material for such a prefilled syringe, for example, a packaging material disclosed in Japanese Patent Application Publication No. 2010-110339 A.

In a medical prefilled syringe package of Japanese Patent Application Publication No. 2010-110339 A, in order to help prevent breakage of the prefilled syringe during transportation or the like, the prefilled syringe is stored in a packaging material including a corrugated cushioning material having a length capable of surrounding a spout portion of the prefilled syringe and an entire length of a syringe barrel.

The package of Japanese Patent Application Publication No. 2010-110339 A is useful in that it is possible to prevent breakage of a predetermined portion of the prefilled syringe during transportation or the like.

However, as a result of further study of the packaging material for a prefilled syringe, it has been found that there is a possibility that the plunger unintentionally presses the gasket or the plunger floats from a predetermined storage position by applying force to the plunger during transportation or the like.

SUMMARY

A prefilled syringe storage tray is disclosed that can simultaneously help prevent the plunger from pressing the gasket and the plunger from floating from a predetermined storage position in a state in which the prefilled syringe is stored, and a package using the prefilled syringe storage tray.

A prefilled syringe storage tray is disclosed that stores a prefilled syringe, which includes: a syringe body including a body flange protruding outward at a proximal end portion; a sealing member sealing a distal end opening portion of the syringe body; a gasket slidably stored in the syringe body; a medicine stored in the syringe body; and a plunger for moving the gasket, which includes a gasket pressing portion provided at a distal end, a pressing operation portion provided at a proximal end, and a shaft portion connecting the gasket pressing portion with the pressing operation portion, the prefilled syringe being formed by disposing a part of the shaft portion of the plunger and the pressing operation portion on a proximal end side with respect to the syringe body, and the prefilled syringe storage tray including a base portion and a proximal end side storage portion that stands upright from the base portion and stores at least the part of the shaft portion of the plunger, in which the proximal end side storage portion includes a shaft portion insertion port for inserting the part of the shaft portion of the plunger, and a pair of insertion port forming portions which are disposed to face a portion which is a side upper portion of the part of the shaft portion of the plunger stored in the proximal end side storage portion and define facing inner edges of the shaft portion insertion port, the proximal end side storage portion includes a protruding piece extending from the inner edge of each of the insertion port forming portions toward the inner edge of the other insertion port forming portion, a first contact portion which is disposed at a first end of the shaft portion insertion port in an axial direction and with which a proximal end surface of the body flange is capable of coming into contact, and a second contact portion which is disposed at a second end facing the first end of the shaft portion insertion port in the axial direction and with which a distal end surface of the pressing operation portion is capable of coming into contact, a distance between the facing inner edges of a pair of the insertion port forming portions is greater than a width of the part of the shaft portion of the plunger, and a distance between the facing inner edges of the insertion port forming portions in a forming portion of the protruding piece is smaller than a width of the part of the shaft portion of the plunger, and when at least the part of the shaft portion of the plunger is stored in the proximal end side storage portion, the proximal end side storage portion supports the syringe body and the plunger in a state in which the syringe body and the plunger cannot approach each other since the first contact portion comes into contact with the proximal end surface of the body flange and the second contact portion comes into contact with the distal end surface of the pressing operation portion, and the part of the shaft portion of the plunger is prevented from separating from the proximal end side storage portion since the protruding piece comes into contact with the part of the shaft portion of the plunger.

In accordance with an aspect, a prefilled syringe storage tray configured to store a plurality of prefilled syringes, each of the plurality of prefilled syringes comprising: a syringe body including a body flange protruding outward at a proximal end portion, a sealing member sealing a distal end opening portion of the syringe body, a gasket slidably stored in the syringe body, a medicine stored in the syringe body, and a plunger for moving the gasket, which includes a gasket pressing portion provided at a distal end, a pressing operation portion provided at a proximal end, and a shaft portion connecting the gasket pressing portion with the pressing operation portion, the prefilled syringe being formed of disposing a part of the shaft portion of the plunger and the pressing operation portion on a proximal end side with respect to the syringe body, the prefilled syringe storage tray comprising: a base portion and a plurality of proximal end side storage portion that stands upright from the base portion, each of the plurality of proximal end side storage portions configured to store at least the part of the shaft portion of the plunger of one prefilled syringe of the plurality of prefilled syringes; the each of the plurality of proximal end side storage portions includes a shaft portion insertion port for inserting the part of the shaft portion of the plunger, and a pair of insertion port forming portions which are disposed to face a portion which is a side upper portion of the part of the shaft portion of the plunger stored in the proximal end side storage portion and define facing inner edges of the shaft portion insertion port; the each of the plurality of proximal end side storage portions further includes a protruding piece extending from the inner edge of each of the insertion port forming portions toward the inner edge of the other insertion port forming portion, a first contact portion which is disposed at a first end of the shaft portion insertion port in an axial direction and with which a proximal end surface of the body flange is capable of coming into contact, and a second contact portion which is disposed at a second end facing the first end of the shaft portion insertion port in the axial direction and with which a distal end surface of the pressing operation portion is capable of coming into contact; a distance between the facing inner edges of a pair of the insertion port forming portions is greater than a width of the part of the shaft portion of the plunger, and a distance between the facing inner edges of the insertion port forming portions in a forming portion of the protruding piece is smaller than a width of the part of the shaft portion of the plunger; and when at least the part of the shaft portion of the plunger is stored in the proximal end side storage portion, the proximal end side storage portion supports the syringe body and the plunger in a state in which the syringe body and the plunger cannot approach each other since the first contact portion comes into contact with the proximal end surface of the body flange and the second contact portion comes into contact with the distal end surface of the pressing operation portion, and the part of the shaft portion of the plunger is prevented from separating from the proximal end side storage portion since the protruding piece comes into contact with the part of the shaft portion of the plunger.

In accordance with another aspect, a package comprising: a prefilled syringe, the prefilled syringe comprising: a syringe body including a body flange protruding outward at a proximal end portion, a sealing member sealing a distal end opening portion of the syringe body, a gasket slidably stored in the syringe body, a medicine stored in the syringe body, and a plunger for moving the gasket, which includes a gasket pressing portion provided at a distal end, a pressing operation portion provided at a proximal end, and a shaft portion connecting the gasket pressing portion with the pressing operation portion, the prefilled syringe being formed of disposing a part of the shaft portion of the plunger and the pressing operation portion on a proximal end side with respect to the syringe body; a prefilled syringe storage tray comprising: a base portion and a proximal end side storage portion that stands upright from the base portion and stores at least the part of the shaft portion of the plunger; wherein the proximal end side storage portion includes a shaft portion insertion port for inserting the part of the shaft portion of the plunger, and a pair of insertion port forming portions which are disposed to face a portion which is a side upper portion of the part of the shaft portion of the plunger stored in the proximal end side storage portion and define facing inner edges of the shaft portion insertion port; the proximal end side storage portion includes a protruding piece extending from the inner edge of each of the insertion port forming portions toward the inner edge of the other insertion port forming portion, a first contact portion which is disposed at a first end of the shaft portion insertion port in an axial direction and with which a proximal end surface of the body flange is capable of coming into contact, and a second contact portion which is disposed at a second end facing the first end of the shaft portion insertion port in the axial direction and with which a distal end surface of the pressing operation portion is capable of coming into contact; a distance between the facing inner edges of a pair of the insertion port forming portions is greater than a width of the part of the shaft portion of the plunger, and a distance between the facing inner edges of the insertion port forming portions in a forming portion of the protruding piece is smaller than a width of the part of the shaft portion of the plunger; and when at least the part of the shaft portion of the plunger is stored in the proximal end side storage portion, the proximal end side storage portion supports the syringe body and the plunger in a state in which the syringe body and the plunger cannot approach each other since the first contact portion comes into contact with the proximal end surface of the body flange and the second contact portion comes into contact with the distal end surface of the pressing operation portion, and the part of the shaft portion of the plunger is prevented from separating from the proximal end side storage portion since the protruding piece comes into contact with the part of the shaft portion of the plunger; and an outer box that stores the prefilled syringe storage tray in which the prefilled syringe is stored.

A package is disclosed, which includes the prefilled syringe storage tray, the prefilled syringe, and an outer box that stores the prefilled syringe storage tray in which the prefilled syringe is stored.

DETAILED DESCRIPTION

Set forth below with reference to the accompanying drawings is a detailed description of embodiments of a prefilled syringe storage tray and a package using the same. Note that since embodiments described below are preferred specific examples of the present disclosure, although various technically preferable limitations are given, the scope of the present disclosure is not limited to the embodiments unless otherwise specified in the following descriptions.

Figure 1:
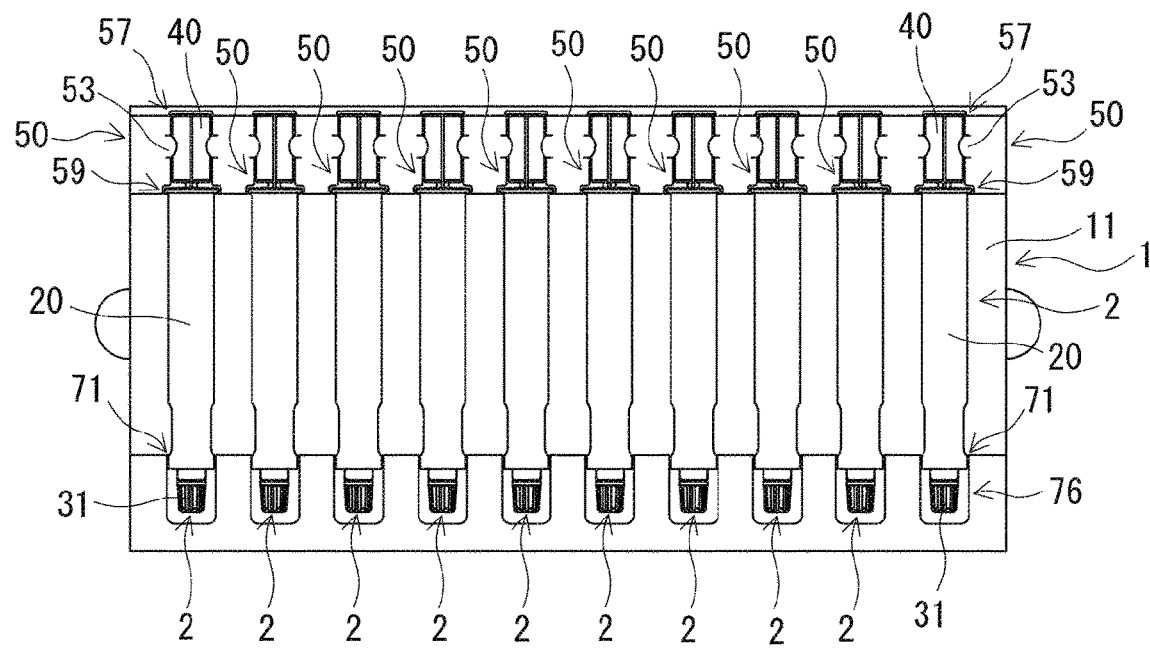
FIG. 1 is a plan view illustrating a state in which a prefilled syringe is stored in a prefilled syringe storage tray according to an example of the present disclosure.
Figure 2:
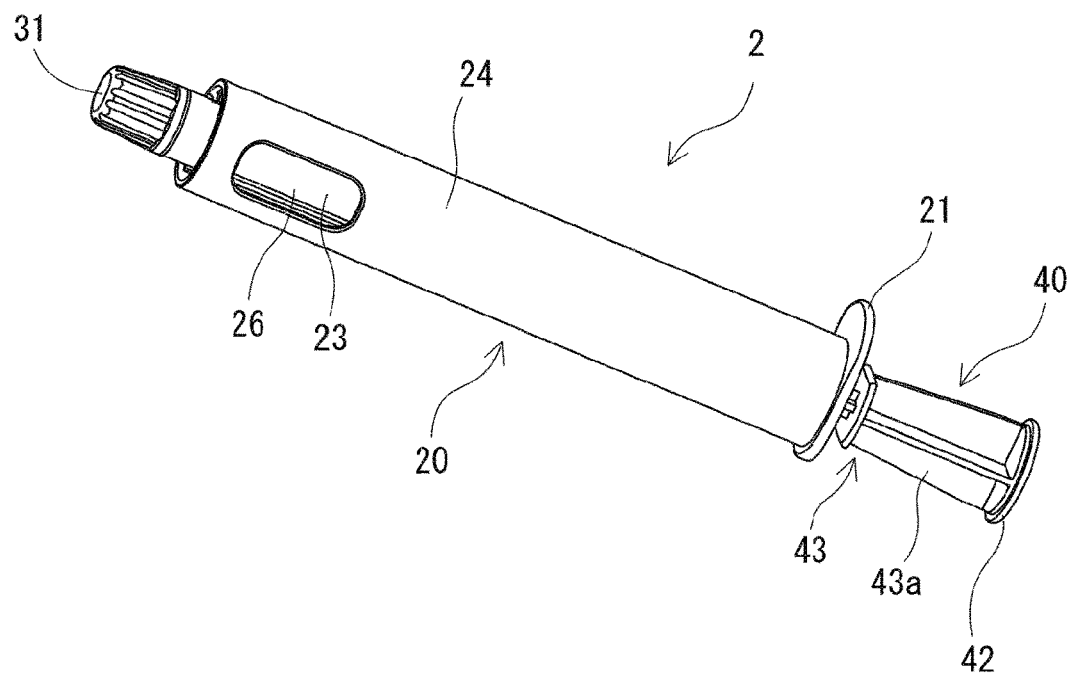
FIG. 2 is a perspective view of a prefilled syringe stored in an example of the present invention.
Figure 3:
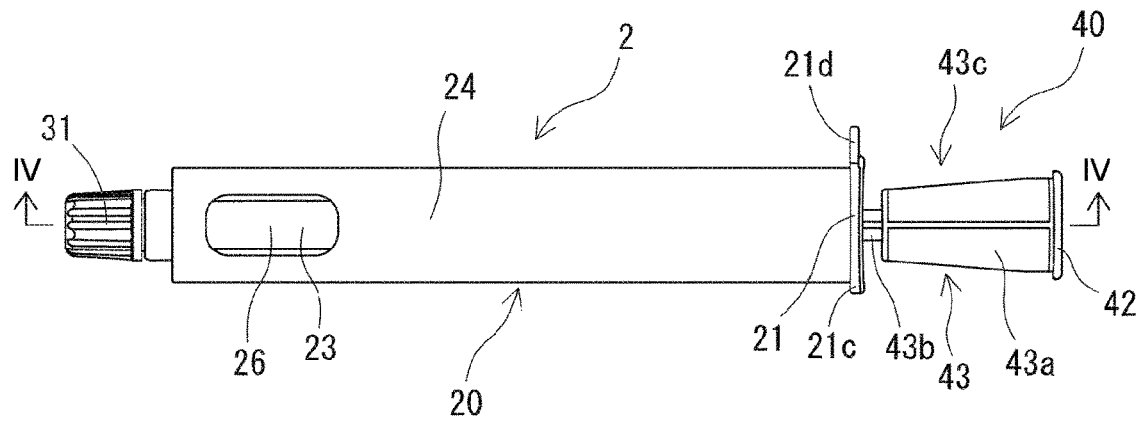
FIG. 3 is a front view of a prefilled syringe stored in an example of the present invention.
Figure 4:
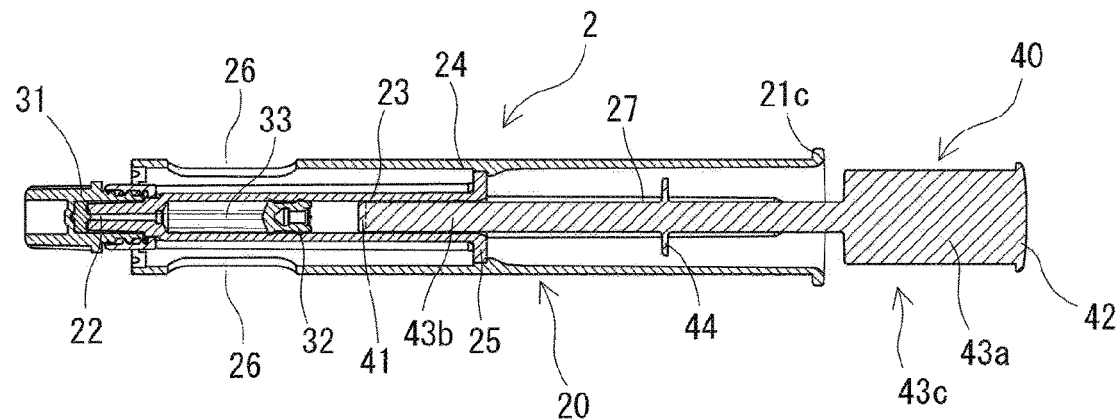
FIG. 4 is a cross-sectional view taken along line IV-IV of FIG. 3.
Figure 5:
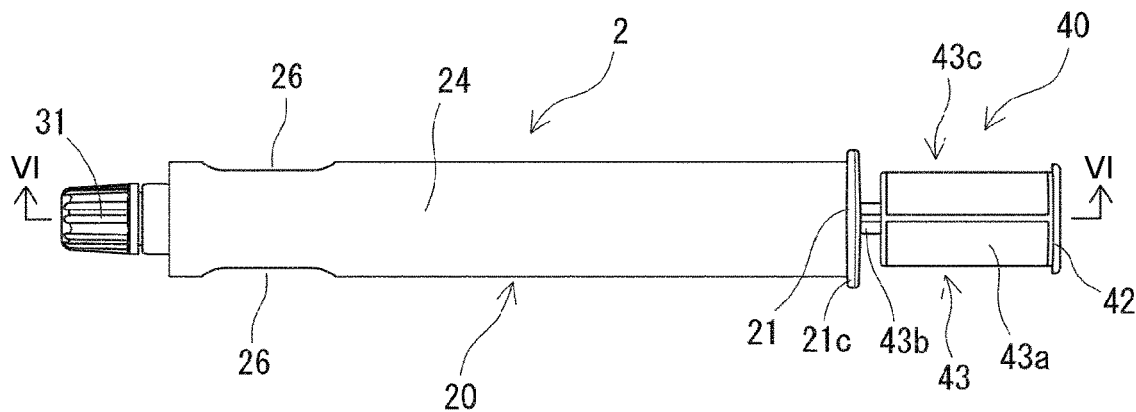
FIG. 5 is a plan view of a prefilled syringe stored in an example of the present invention.
Figure 6:
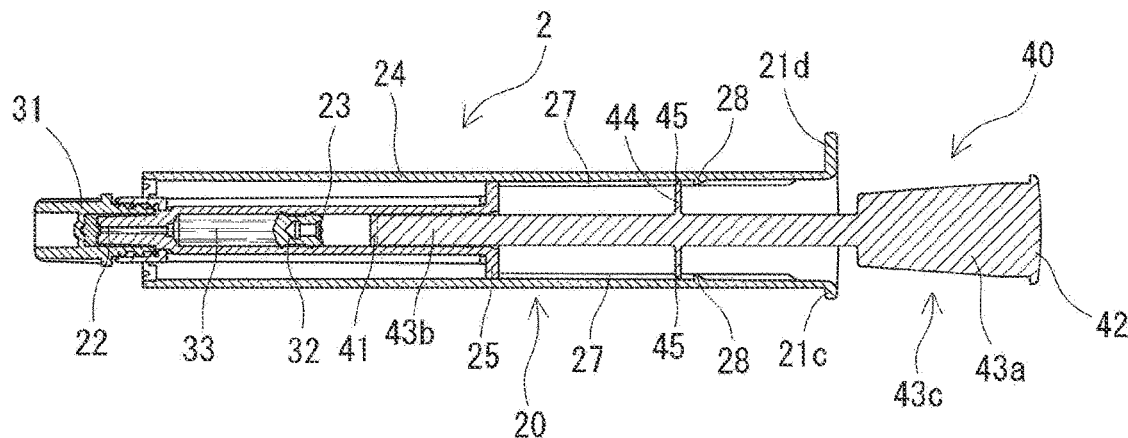
FIG. 6 is a cross-sectional view taken along line VI-VI of FIG. 5.

FIG. 1 is a plan view illustrating a state in which a plurality of prefilled syringes 2 are stored in a prefilled syringe storage tray 1 (hereinafter, also simply referred to as a storage tray 1). In the following description, an upper side (upward direction) in FIG. 1 is referred to as a proximal end side (proximal end direction), and a lower side (downward direction) is referred to as a distal end side (distal end direction).

The storage tray 1 of the present disclosure is a prefilled syringe storage tray 1 that stores the prefilled syringes 2 including: a syringe body 20 having a body flange 21 protruding outward at a proximal end portion, a sealing member 31 sealing a distal end opening portion 22 of the syringe body 20; a gasket 32 slidably stored in the syringe body 20; a medicine 33 stored in the syringe body 20; and a plunger 40 for moving the gasket 32, which includes a gasket pressing portion 41 provided at a distal end, a pressing operation portion 42 provided at a proximal end, and a shaft portion 43 connecting the gasket pressing portion 41 with the pressing operation portion 42. In accordance with an exemplary embodiment, the prefilled syringes 2 can be formed by disposing a part of the shaft portion 43 of the plunger 40 (mainly referred to as a large diameter portion 43a; hereinafter, also referred to as a part 43c of a shaft portion) and the pressing operation portion 42 on a proximal end side with respect to the syringe body 20.

The prefilled syringe storage tray 1 can include a base portion 11 and a proximal end side storage portion 50 that stands upright from the base portion 11 and stores at least a part 43c of the shaft portion of the plunger 40. The proximal end side storage portion 50 includes a shaft portion insertion port 51 for inserting the part 43c of the shaft portion of the plunger 40, and a pair of insertion port forming portions 52 which are disposed to face a portion which is a side upper portion of the part 43c of the shaft portion of the plunger 40 stored in the proximal end side storage portion 50 and define facing inner edges 51a of the shaft portion insertion port 51.

The proximal end side storage portion 50 includes a protruding piece 53 extending from an inner edge (edge defining the inner edges 51a) of each of the insertion port forming portions 52 toward an inner edge of the other insertion port forming portion 52, a first contact portion 54 which is disposed at a first end of the shaft portion insertion port 51 in an axial direction (end portion on a distal end side (a lower end portion in FIG. 1)) and with which a proximal end surface 21a of the body flange 21 can come into contact, and a second contact portion 55 which is disposed at a second end (end portion on a proximal end side (an upper end portion in FIG. 1)) facing the first end of the shaft portion insertion port 51 in the axial direction and with which a distal end surface 42a of the pressing operation portion 42 can come into contact. In accordance with an exemplary embodiment, a distance between the facing inner edges of a pair of the insertion port forming portions 52 is greater than a width of the part 43c of the shaft portion of the plunger 40, and a distance between the facing inner edges of the insertion port forming portions 52 in a forming portion of the protruding pieces 53 is smaller than a width of the part 43c of the shaft portion of the plunger 40.

When at least the part 43c of the shaft portion of the plunger 40 is stored in the proximal end side storage portion 50, the proximal end side storage portion 50 supports the syringe body 20 and the plunger 40 in a state in which the syringe body 20 and the plunger 40 cannot approach each other since the first contact portion 54 comes into contact with the proximal end surface 21a of the body flange 21 and the second contact portion 55 comes into contact with the distal end surface 42a of the pressing operation portion 42, and the part 43c of the shaft portion of the plunger 40 is prevented from separating from the proximal end side storage portion 50 since the protruding pieces 53 come into contact with the part 43c of the shaft portion of the plunger 40.

As illustrated in FIG. 1, the prefilled syringe storage tray 1 includes a plurality of (for example, as shown, ten) proximal end side storage portions 50, and can store a plurality of (for example, as shown, ten) prefilled syringes 2.

Each of the prefilled syringes 2 in the present embodiment will be described with reference to FIGS. 2 to 6.

The syringe body 20 of the prefilled syringe 2 can include a barrel 23 that slidably stores the gasket 32, stores the medicine 33 in the barrel 23, and has the distal end opening portion 22 sealed by the sealing member 31. In addition, the prefilled syringe 2 can include an outer cylinder 24 that stores the barrel 23 and is attached to the barrel 23.

In accordance with an exemplary embodiment, the barrel 23 can be a substantially cylindrical member that stores the gasket 32 liquid-tightly and slidably. A distal end opening portion (nozzle portion) 22 is provided at a distal end portion of the barrel 23. The distal end opening portion 22 is sealed by a sealing member (seal cap) 31.

More specifically, the barrel 23 is a cylindrical member having a diameter smaller than that of the outer cylinder 24, and an axial length of the barrel 23 can be about half of that of the outer cylinder 24. A barrel flange 25 protruding outward is formed at a proximal end portion of the barrel 23. The barrel 23 is stored in the distal end side portion of the outer cylinder 24, and is attached (connected) to an inside of the outer cylinder 24 in the barrel flange 25. According to this, the syringe body 20 of the present embodiment has a double cylinder structure constituted by the barrel 23 and the outer cylinder 24 at the distal end side portion of the syringe body 20.

In accordance with an exemplary embodiment, the outer cylinder 24 is a substantially cylindrical member extending over substantially an entire length of the syringe body 20. A pair of windows 26 communicating the inside and the outside of the outer cylinder 24 is formed at the distal end side portion of the outer cylinder 24 so as to face each other in a radial direction. A part of the barrel 23 stored in the outer cylinder 24 can be visually recognized from the outside through the windows 26.

In accordance with an exemplary embodiment, a rear end side portion of the outer cylinder 24 configures a rear end side portion of the syringe body 20. That is, the rear end side portion of the syringe body 20 has a single cylinder structure configured by the outer cylinder 24. On an inner circumferential surface of the rear end side portion of the syringe body 20 (outer cylinder 24), a pair of guides 27 formed of a pair of linear protrusions extending in parallel with the axial direction is formed to face each other in the radial direction. Moreover, each of protrusions 28 protruding inward is formed in an intermediate portion of each of the guides 27.

The body flange 21 protruding outward (in a direction orthogonal to the axial direction) can be provided at the proximal end portion of the syringe body 20 (outer cylinder 24). The body flange 21 can include a general portion 21c slightly protruding from an outer circumferential surface of the syringe body 20 and a protrusion 21d further protruding from the general portion 21c. Specifically, the protrusion 21d has a shape surrounded by two parallel contact surfaces with respect to the outer circumferential surface of the general portion 21c and an arc surface obtained by offsetting the outer circumferential surface of the general portion 21c further outward by a predetermined distance (see FIG. 16). The protrusion 21d of the body flange 21 protrudes in a direction orthogonal to a direction in which two windows 26 and 26 described above are facing each other.

In accordance with an exemplary embodiment, the gasket 32 can be made, for example, of elastic rubber or a synthetic resin. The gasket 32 includes a substantially cylindrical main body portion extending with substantially the same outer diameter and a plurality of annular ribs provided on an outer surface of the main body portion, and outer side surfaces of the annular ribs are in liquid-tight contact with an inner surface of the barrel 23.

In the syringe body 20 (barrel 23), a space formed between the sealing member 31 and the gasket 32 can be filled with a medicine (liquid medicine) 33 in advance. As the medicine 33 to be filled here, a medicine used for an intradermal injection is suitable, and examples of the medicine include various vaccines for preventing various infectious diseases such as influenza, carbohydrate injection solutions such as glucose, injection solutions for electrolyte correction such as sodium chloride and potassium lactate, vitamins, antibiotic injection solutions, contrast agents, steroid agents, protease inhibitors, fat emulsions, anticancer agents, anesthetics, heparin calcium, an antibody medicine, hyaluronic acid, and the like.

In accordance with an exemplary embodiment, the plunger 40 can be made, for example, of a hard or semi-hard resin. In this example, the plunger 40 can include the gasket pressing portion 41 provided at the distal end, the disk-shaped pressing operation portion 42 provided at the proximal end, and a shaft portion 43 formed in a cross-shaped cross section. Moreover, in the shaft portion 43, a rear end side portion (here, for example, about ¼ of an entire length) is a large diameter portion 43a, and a distal end side portion (here, for example, about ¾ of an entire length) is a small diameter portion 43b. The pressing operation portion 42 is formed at a proximal end of the shaft portion 43 (proximal end of the large diameter portion 43a) with a diameter larger than that of the large diameter portion 43a.

The small diameter portion 43b of the shaft portion 43 of the plunger 40 is formed to be insertable into the barrel 23. The disk-shaped gasket pressing portion 41 capable of coming into contact with a proximal end of the gasket 32 is formed at a distal end of the small diameter portion 43b (distal end of the shaft portion 43). In accordance with an exemplary embodiment, the plunger 40 (gasket pressing portion 41) and the gasket 32 are not integrally fixed (i.e., not connected together so as to make up a single complete piece or unit.

FIGS. 2 to 6 illustrate a state in which the prefilled syringe 2 is stored in the storage tray 1, and wherein a part of the shaft portion 43 of the plunger 40 is disposed on the proximal end side of the syringe body 20 together with the pressing operation portion 42. In accordance with an exemplary embodiment, a portion of the shaft portion 43, which is disposed on the proximal end side of the syringe body 20 (portion on the proximal end side of the large diameter portion 43a and the small diameter portion 43b), is a part 43c of the shaft portion.

Furthermore, an intermediate flange 44 protruding radially outward can be provided at an axially intermediate portion of the small diameter portion 43b, the axially intermediate portion being on the distal end side with respect to the protrusion 28 formed in the syringe body 20 (outer cylinder 24). In addition, a pair of protruding pieces 45 protruding radially outward can be formed on the intermediate flange 44 so as to face each other in the radial direction. Each of the protruding pieces 45 is stored in the guide 27 described above (between a pair of linear protrusions) in a slidable manner in the axial direction, and are formed to have a size capable of coming into contact with the protrusions 28. According to this, a rotation of the plunger 40 about a central axis can be restricted, and a movement of the plunger 40 in a proximal end direction (direction away from the syringe body 20) can be restricted by the contact between the protruding piece 45 and the protrusion 28.

In a case where the medicine 33 is discharged by using the prefilled syringe 2 described above, first, a distal end of the plunger 40 (gasket pressing portion 41) is brought into contact with the proximal end of the gasket 32 in a state in which the distal end opening portion 22 communicates with the outside. Next, the plunger 40 and the gasket 32 are integrally moved (i.e., connected together so as to make up a single complete piece or unit) in the distal end direction by pressing the pressing operation portion 42 of the plunger 40. According to this, the medicine 33 is extruded (discharged) from the distal end opening portion 22 of the syringe body 20 (barrel 23). At this time, in addition to the outer circumferential surface of the syringe body 20 (outer cylinder 24), the body flange 21 (for example, the protrusion 21d) may be held.

A structure of the storage tray 1 will be described with reference to FIG. 1, and FIGS. 7 to 13. Note that, a vertical direction in FIG. 9 will be described as a vertical direction of the storage tray 1. Furthermore, in FIG. 9, in order to describe an overlapping state and a bent state of each part in the storage tray 1, a thickness of a sheet 10 configuring the storage tray 1 is enlarged and the prefilled syringe 2 to be stored later is indicated by a broken line.

Figure 7:
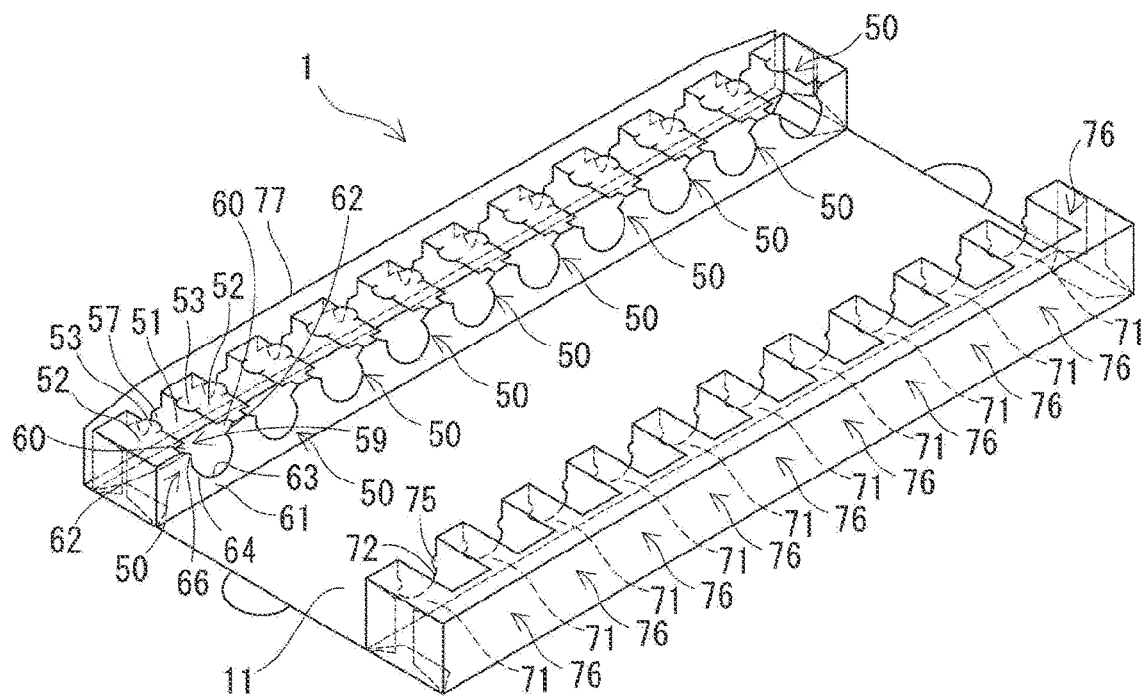
FIG. 7 is a perspective view of a prefilled syringe storage tray of an example of the present disclosure.
Figure 11:
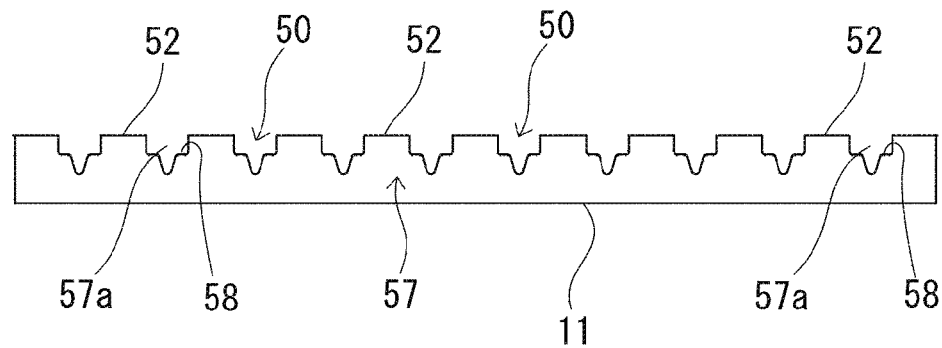
FIG. 11 is an explanatory view for explaining a second end side of a proximal end side storage portion of a prefilled syringe storage tray of an example of the present disclosure.
Figure 12:
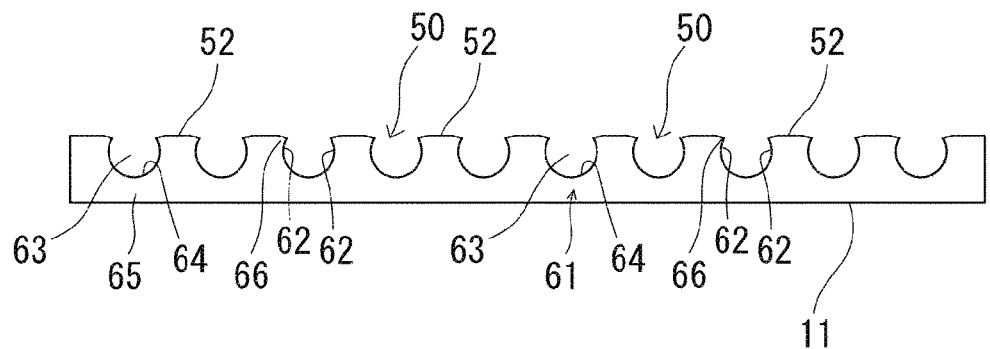
FIG. 12 is an explanatory view for explaining a first end side of a proximal end side storage portion of a prefilled syringe storage tray of an example of the present disclosure.

In accordance with an exemplary embodiment, the storage tray 1 can include a rectangular plate-shaped base portion 11 over the entire lower portion of the storage tray 1. As illustrated in FIGS. 7, 11, and 12, the standing proximal end side storage portion 50 is provided in a proximal end side portion of the base portion 11. The proximal end portion storage portion 50 is provided with the shaft portion insertion port 51 for inserting the part 43c of the shaft portion of the plunger 40 so as to be open upward.

Figure 8:
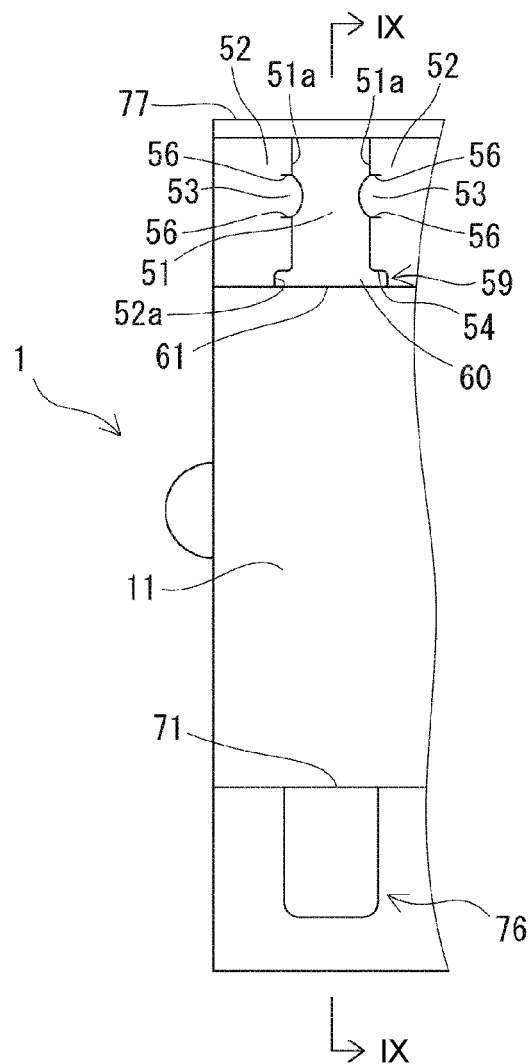
FIG. 8 is a partially enlarged plan view of a prefilled syringe storage tray of an example of the present disclosure.
Figure 9:
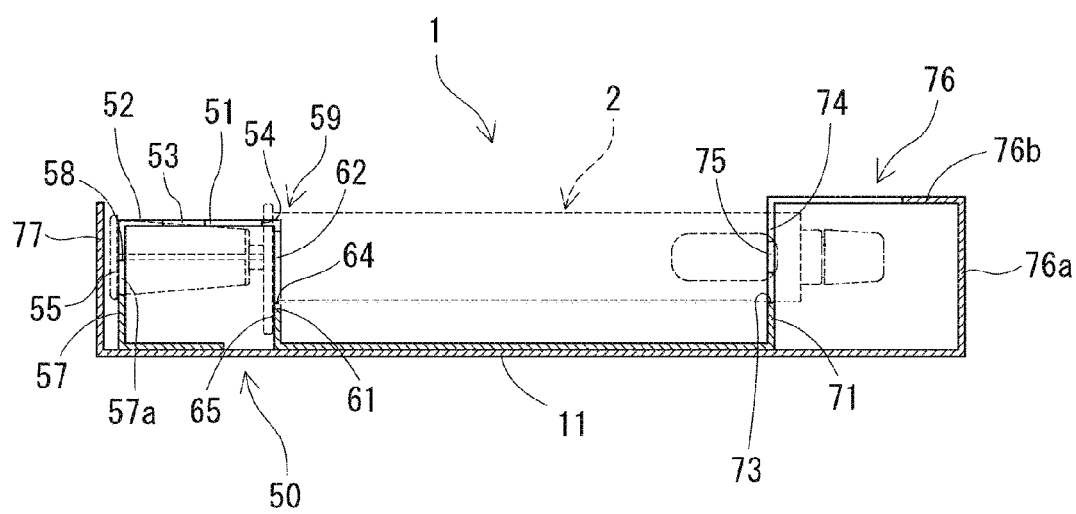
FIG. 9 is a cross-sectional view taken along line IX-IX of FIG. 8.

As illustrated in FIGS. 1 and 7, the proximal end side storage portion 50 includes a pair of the insertion port forming portions 52 disposed to face each other on an upper portion of the proximal end side storage portion 50, and the shaft portion insertion port 51 is formed between a pair of the insertion port forming portions 52. As illustrated in FIGS. 8 and 9, a pair of the insertion port forming portions 52 can be plate-like portions extending substantially in parallel with the base portion 11. The inner edges of the insertion port forming portions 52 (edges of a pair of the insertion port forming portions 52 on sides facing each other) configures the inner edges 51a of the shaft portion insertion port 51.

Each of the protruding pieces 53 extending toward each of the inner edges of the insertion port forming portions 52 facing each other is formed at each of the inner edges of a pair of the insertion port forming portions 52. In accordance with an exemplary embodiment, the two protruding pieces 53 and 53 are formed so as to face each other (at the same positions in the extending direction of the insertion port forming portion 52), but the two protruding pieces 53 and 53 may be formed at positions shifted in the extending direction of the insertion port forming portion 52. Furthermore, notches 56 are formed at both side portions of the protruding piece 53 of the insertion port forming portion 52. In this example, each of the notches 56 is continuous with an outer edge of the protruding piece 53 and extends in a direction opposite to the protruding piece 53. According to this, temporary elastic deformation of the protruding piece 53 can be rather easily performed, and a storage operation and a removal operation of the prefilled syringe 2 can also be rather easily performed.

As illustrated in FIGS. 7, 9, and 11, a plate-like erected connection portion 57 (erected from the base portion 11) is provided at an end portion (second end) of the shaft portion insertion port 51 in the proximal end direction. The erected connection portion 57 connects end portions of a pair of the insertion port forming portions 52 on the second end (proximal end) side. In this example, the proximal end side storage portion 50 includes the erected connection portion 57 erected from the base portion 11, and the erected connection portion 57 includes the second contact portion 55 with which a distal end surface (surface on the distal end side) 42a of the pressing operation portion 42 can come into contact, and connects end portions (end portions in the proximal end direction) of a pair of the insertion port forming portions 52 with the base portion 11.

Figure 15:
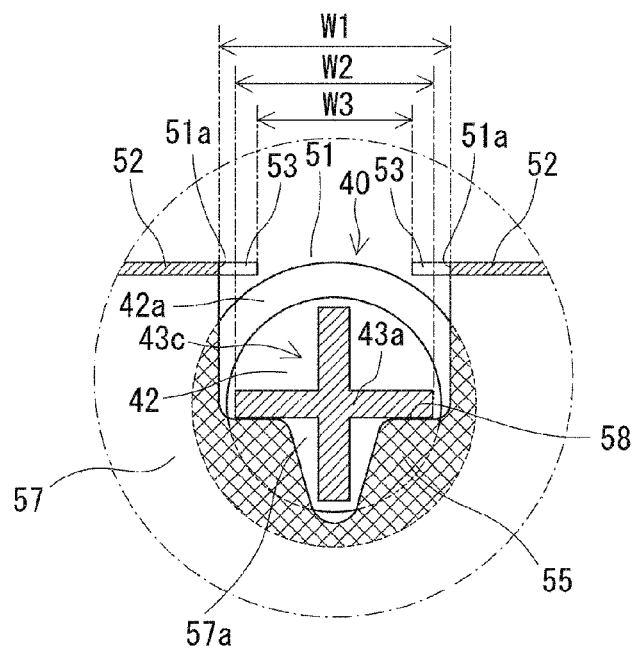
FIG. 15 is a cross-sectional view taken along line XV-XV of FIG. 14.

As illustrated in FIGS. 11 and 15, a shaft insertion cutout portion 57a is formed in the erected connection portion 57. In accordance with an exemplary embodiment, the shaft insertion cutout portion 57a has a stepped shape, and a step portion of the shaft insertion cutout portion 57a is a shaft portion contact portion 58 capable of supporting the shaft portion 43 (large diameter portion 43a) of the plunger 40. The erected connection portion 57 includes the shaft portion contact portion 58 that supports the shaft portion 43.

As illustrated in FIGS. 1 and 7, the proximal end side storage portion 50 includes a body flange storage portion 59 which is adjacent to ends of a pair of the insertion port forming portions 52 and stores the body flange 21. The body flange storage portion 59 includes a flange insertion port 60 that communicates with the shaft portion insertion port 51 and is for inserting the body flange 21, a proximal end side support portion 61 that is erected from the base portion 11 and supports a portion in the vicinity of the body flange 21 of the syringe body 20, and two extending portions 62 and 62 that extend from end portions of a pair of the insertion port forming portions 52 on the end portion (first end) side of the shaft portion insertion port 51 in the distal end direction to an erected end on a side opposite to the base portion 11 of the proximal end side support portion 61 and define inner edges of both side portions of the flange insertion port 60. In the storage tray 1, as illustrated in FIG. 8, cutout portions 52a configuring the body flange storage portion 59 (flange insertion port 60) are formed at distal end portions of the insertion port forming portions 52. In accordance with an exemplary embodiment, a width (dimension in a right-left direction in FIG. 8) of the flange insertion port 60 can be equal to or slightly larger than a diameter of the general portion 21c of the body flange 21 and smaller than that of the protrusion 21d.

Figure 13:
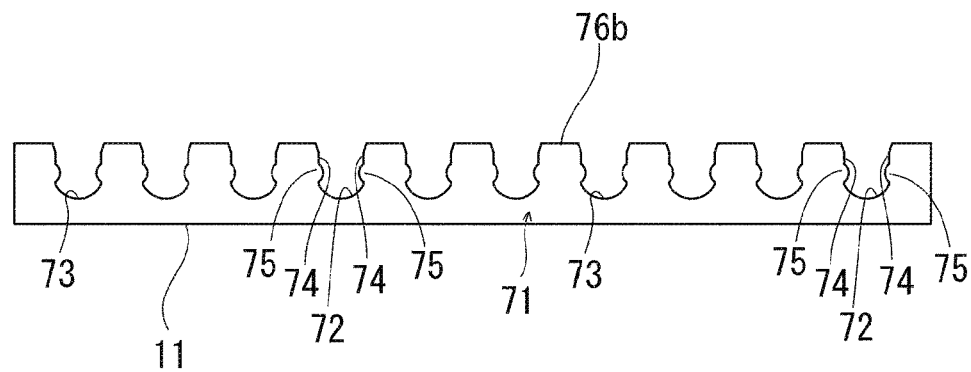
FIG. 13 is an explanatory view for explaining a distal end side support portion of a prefilled syringe storage tray of an example of the present disclosure.

As illustrated in FIGS. 1, 7, and 13, the prefilled syringe storage tray 1 includes a distal end side support portion 71 that is erected from the base portion 11 and supports a distal end portion of the syringe body 20 in a distal end side portion of the prefilled syringe storage tray 1. The distal end side support portion 71 can be a plate-like portion erected from the base portion 11.

As illustrated in FIG. 13, the distal end side support portion 71 is opened toward an erected end (upward) on a side opposite to the base portion 11 of the distal end side support portion 71, and can include a substantially U-shaped distal end side cutout portion 72 to which the distal end portion of the syringe body 20 can be inserted. A bottom portion (lower portion of an inner edge portion) of the distal end side cutout portion 72 defines a distal end side contact portion 73 that can be brought into contact with the distal end portion of the syringe body 20. The distal end side cutout portion 72 includes a bottom portion defining the distal end side contact portion 73 and a pair of side portions 74 facing each other, and a pair of the side portions 74 include engagement protrusions 75 protruding in a direction in which a pair of the side portions 74 approach each other. In accordance with an exemplary embodiment, when the distal end portion of the syringe body 20 is inserted into the distal end side cutout portion 72 by bringing the distal end side contact portion 73 into contact with the distal end portion of the syringe body 20, the distal end side support portion 71 supports the distal end portion of the syringe body 20, the engagement protrusions 75 are engaged with the distal end portion of the syringe body 20 (here, the windows 26 formed at the distal end portion of the syringe body 20), and removal of the syringe body 20 from the distal end side cutout portion 72 can be restricted.

As illustrated in FIG. 1 and FIGS. 7 to 9, the prefilled syringe storage tray 1 includes a distal end side storage portion 76 that is adjacent to the distal end side support portion 71 and stores at least the sealing member 31. As illustrated in FIG. 9, the distal end side storage portion 76 can include a side wall portion 76a erected from a distal end side end portion of the base portion 11 and an upper wall portion 76b extending in the proximal end direction from an upper end portion of the side wall portion 76a. The upper wall portion 76b is provided with a cutout that communicates with the distal end side cutout portion 72 and is opened upward, so that the distal end portion (including the sealing member 31) of the prefilled syringe 2 can be stored from above the distal end side storage portion 76.

In the storage tray 1, as illustrated in FIGS. 1, 7, and 9, an erected wall portion 77 erected from the base portion 11 is provided at an end portion of the storage tray 1 in the proximal end direction. The erected wall portion 77 is provided at a predetermined distance from the above-described erected connection portion 57 (for example, a distance larger than a thickness of the pressing operation portion 42 of the plunger 40). According to this, a space between the erected wall portion 77 and the erected connection portion 57 also functions as a buffer space for the plunger 40. Furthermore, in the vertical direction, the erected wall portion 77 can be higher than the proximal end side storage portion 50 and extends up to the same height as that of the distal end side storage portion 76. According to this, when the storage tray 1 is stored in an outer box 90, the movement of the storage tray 1 of the outer box 90 in the vertical direction, that is, so-called rattling is restricted on both the distal end side and the proximal end side of the tray.

Figure 10:
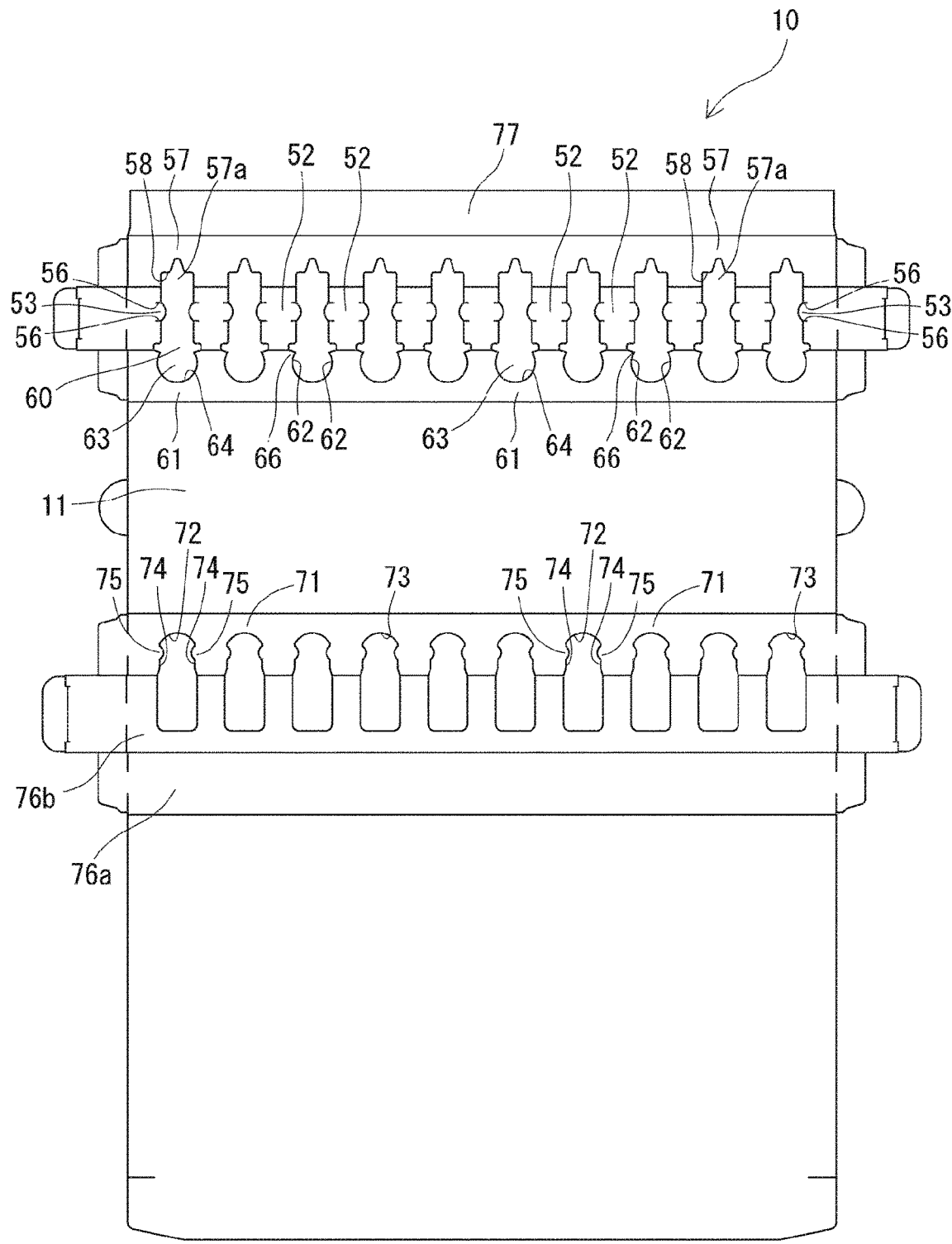
FIG. 10 is a plan view of a sheet constituting a prefilled syringe storage tray of an example of the present disclosure.

Note that, in the present embodiment, the storage tray 1 is configured by one sheet. In FIG. 10, one sheet 10 capable of configuring the storage tray 1 is illustrated in an unfolded state (cut-out and unfolded state). A basic configuration of the sheet 10 is formed by partially cutting and punching one laterally long sheet (for example, paperboard or cardboard). In FIG. 10, with respect to the sheet 10, the same reference numerals are given to portions corresponding to the configuration of the storage tray 1.

Figure 14:
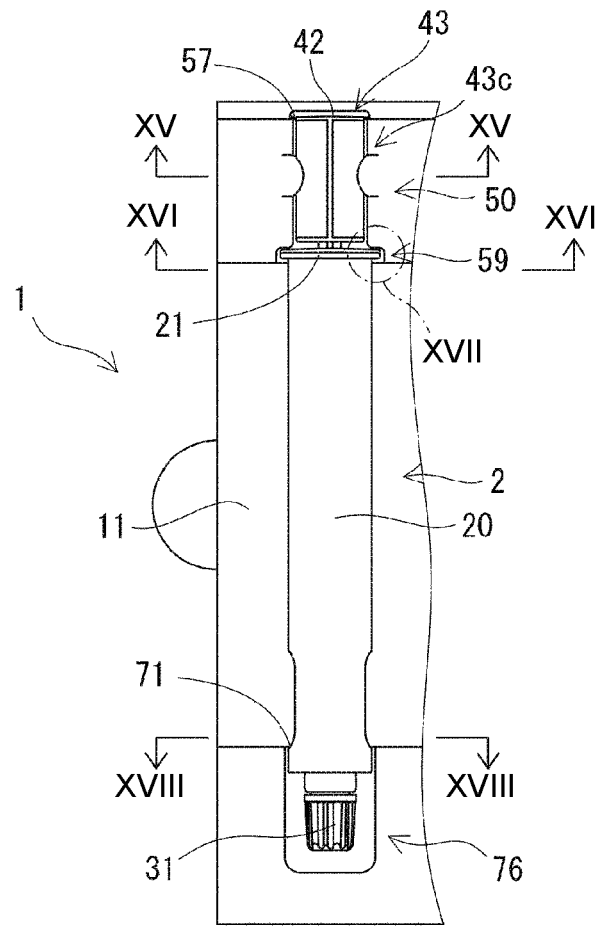
FIG. 14 is a partially enlarged explanatory view of FIG. 1.

A state when the prefilled syringe 2 is stored in the storage tray 1 and a state in which the prefilled syringe 2 is stored in the storage tray 1 will be described with reference to FIGS. 14 to 18. Note that, in FIGS. 15, 16, and 18, some configurations are omitted in order to efficiently describe the example. In accordance with an exemplary embodiment, the prefilled syringe 2 can be pushed into and stored in the storage tray 1 from above. Specifically, as illustrated in FIG. 14, the part 43c of the shaft portion, the body flange 21 of the syringe body 20, and the portion in the vicinity of the body flange 21 of the syringe body 20 are stored in the proximal end side storage portion 50, the distal end portion of the syringe body 20 is supported by the distal end side support portion 71, and the sealing member 31 is stored in the distal end side storage portion 76. In accordance with an exemplary embodiment, when the prefilled syringe 2 is stored, the protrusion 21d of the body flange 21 is directed downward (toward the storage tray 1), and the pressing operation portion 42 of the plunger 40 is positioned in the proximal end direction with respect to the erected connection portion 57. In the example, since a width of the body flange storage portion 59 (flange insertion port 60) is equal to or slightly larger than the diameter of the general portion 21c of the body flange 21 and smaller than the diameter of the protrusion 21d, it can be rather easy to determine a direction at the time of storing the syringe body 20 with the protrusion 21d of the body flange 21 directed downward.

Here, as illustrated in FIG. 15, a distance W1 between the facing inner edges of a pair of the insertion port forming portions 52 (inner edges 51a of the shaft portion insertion port 51) is larger than a width W2 of the part 43c of the shaft portion of the plunger 40 (large diameter portion 43a). Furthermore, a distance W3 between the facing inner edges of the insertion port forming portions 52 in the forming portion of the protruding pieces 53 (here, between the two protruding pieces 53 and 53 formed so as to face each other) is smaller than the width W2 of the part 43c of the shaft portion of the plunger 40 (large diameter portion 43a). Therefore, when the prefilled syringe 2 is stored in the storage tray 1, the part 43c of the shaft portion is brought into contact with the protruding pieces 53 to be further pushed, and the protruding pieces 53 can be temporarily deformed (elastically deformed).

As illustrated in FIG. 15, the part 43c of the shaft portion stored in the proximal end side storage portion 50 is brought into contact with and supported by the shaft portion contact portion 58 formed in the erected connection portion 57. Furthermore, the pressing operation portion 42 of the plunger 40 disposed further in the proximal end direction with respect to the erected connection portion 57 comes into contact with the erected connection portion 57 or is disposed with a slight gap interposed between the pressing operation portion 42 of the plunger and the erected connection portion 57. That is, the second contact portion 55 with which the distal end surface 42a of the pressing operation portion 42 can come into contact is formed in a portion overlapping with the pressing operation portion 42 of the erected connection portion 57 (cross hatched portion in FIG. 15) when viewed from the axial direction. According to this, in a state in which the prefilled syringe 2 is stored in the storage tray 1, the movement of the plunger 40 in the distal end direction (direction approaching the syringe body 20) can be restricted.

Figure 16:
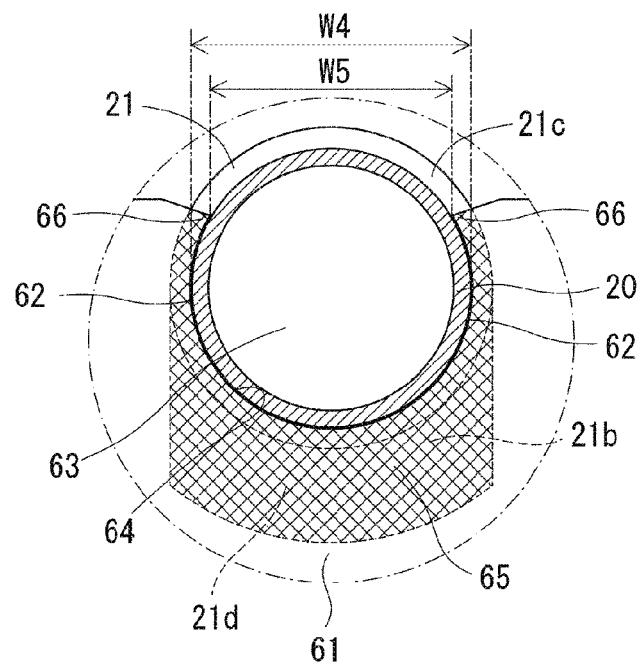
FIG. 16 is a cross-sectional view taken along line XVI-XVI of FIG. 14.

As illustrated in FIGS. 7, 12, and 16, the proximal end side support portion 61 of the body flange storage portion 59 includes: a substantially U-shaped proximal end side cutout portion 63 which connects the two extending portions 62 and 62 to each other, is opened toward an erected end (upper side) of the proximal end side support portion 61, and into which the portion in the vicinity of the body flange 21 of the syringe body 20 is capable of being inserted; a proximal end side contact portion 64 formed by a portion defining an inner edge of the proximal end side cutout portion 63; and a movement restriction portion 65 provided at a portion connecting the proximal end side contact portion 64 with the base portion 11. When the portion in the vicinity of the body flange 21 of the syringe body 20 is inserted into the proximal end side cutout portion 63, the proximal end side contact portion 64 comes into contact with the portion in the vicinity of the body flange 21 of the syringe body 20, and the movement restriction portion 65 comes into contact with a distal end surface 21b of the body flange 21 to restrict the movement of the syringe body 20 in the distal end direction.

In other words, the distal end surface 21b of the body flange 21 comes into contact with the proximal end side support portion 61 or is disposed with a slight gap interposed between the distal end surface 21b of the body flanged 21 and the proximal end side support portion 61 in the proximal end direction with respect to the proximal end side support portion 61, and the movement restriction portion 65 that comes into contact with the distal end surface 21b of the body flange 21 to restrict the movement of the syringe body 20 in the distal end direction is in a portion overlapping with the body flange 21 of the proximal end side support portion 61 (cross hatched portion in FIG. 16) when viewed from the axial direction.

Furthermore, as illustrated in FIGS. 7, 12, and 16 (in particular, FIG. 16), the proximal end side contact portion 64 includes a narrowed portion 66 (width W5) in which the width of the proximal end side cutout portion 63 is narrower than a diameter W4 of the syringe body 20. When the portion in the vicinity of the body flange 21 of the syringe body 20 is inserted into the proximal end side cutout portion 63, the narrowed portion 66 is engaged with the portion in the vicinity of the body flange 21 of the syringe body 20 to help restrict removal (upward movement) of the portion in the vicinity of the body flange 21 of the syringe body 20 from the proximal end side cutout portion 63.

Figure 17:
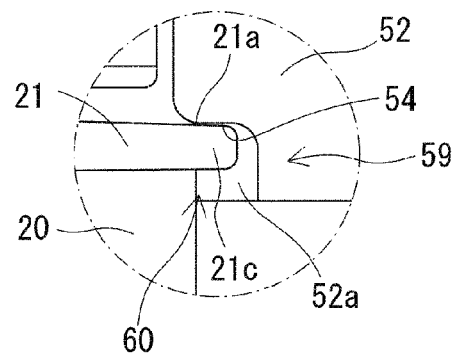
FIG. 17 is an enlarged explanatory view of a portion XVII of FIG. 14.
Figure 18:
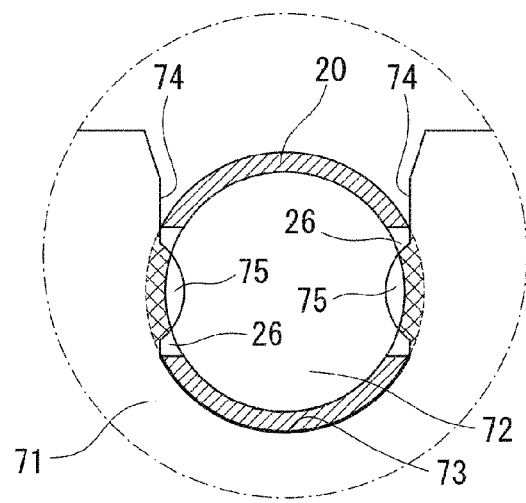
FIG. 18 is a cross-sectional view taken along line XVIII-XVIII of FIG. 14.

The body flange 21 is stored in the body flange storage portion 59. More specifically, as illustrated in FIG. 17, the general portion 21c of the body flange 21 is stored in the cutout portion 52a configuring the body flange storage portion 59. The width (dimension in the vertical direction in FIG. 17) of the cutout portion 52a can be equal to or slightly larger than a thickness of the general portion 21c of the body flange 21, and the surface of the cutout portion 52a exposed in the distal end direction and the proximal end surface 21a of the body flange 21 (general portion 21c) are in contact with each other or face each other with a slight gap. That is, in the body flange storage portion 59, a portion facing the proximal end surface 21a of the body flange 21, here, the first contact portion 54 with which the proximal end surface 21a of the body flange 21 comes into contact is configured by a surface of the cutout portion 52a formed in the insertion port forming portion 52, the surface being exposed in the distal end direction. According to this, in a state in which the prefilled syringe 2 is stored in the storage tray 1, the movement of the syringe body 20 in the proximal end direction (direction approaching the plunger 40) can be restricted.

As illustrated in FIGS. 1, 7, 9, 13, and 18 (in particular, FIG. 18), the distal end portion of the syringe body 20 is inserted into the distal end side cutout portion 72 formed in the distal end side support portion 71 of the storage tray 1, and is supported by being brought into contact with the distal end side contact portion 73 (bottom portion of the distal end side cutout portion 72). In this state, the engagement protrusions 75 formed on a pair of the side portions 74 of the distal end side cutout portion 72 enter the windows 26 formed at the distal end portion of the syringe body 20. According to this, removal of the syringe body 20 from the distal end side cutout portion 73 can be restricted.

Furthermore, distal end surfaces of the engagement protrusions 75 comes into contact with the surfaces of the windows 26 exposed in the proximal end direction or is disposed with a slight gap interposed between the distal end surfaces of the engagement protrusions 75 and the surfaces of the windows 26 exposed in the proximal end direction. Therefore, when viewed from the axial direction, the movement of the syringe body 20 in the proximal end direction is restricted in portions (cross hatched portion in FIG. 18) overlapping with the surfaces of the engagement protrusion 75 exposed in the proximal end direction of the windows 26 (end surface of the syringe body 20).

In the storage tray 1, the proximal end side storage portion 50 stores at least the part 43c of the shaft portion of the plunger 40 in a state in which the gasket pressing portion 41 of the plunger 40 is not in contact with the gasket 42 (state illustrated in FIGS. 2 to 6). Furthermore, as described above, the prefilled syringe 2 can be held at a predetermined interval (floating) from the base portion 11 of the storage tray 1 such that the syringe body 20 can be suspended between the proximal end side support portion 61 and the distal end side support portion 71. According to this, in the stored state, a buffering effect against an impact (force) applied via the base portion 11 is exerted.

In the storage tray 1, when the proximal end side storage portion 50 stores at least the part 43c of the shaft portion of the plunger, the protruding pieces 53 exist above the part 43c of the shaft portion of the plunger 40 (when viewed from above, the protruding pieces 53 and the part 43c of the shaft portion at least partially overlap with each other). Therefore, since the part 43c of the shaft portion comes into contact with the protruding pieces 53, the part 43c of the shaft portion of the plunger 40 can be prevented from being removed from the proximal end side storage portion 50. According to this, the plunger 40 can be prevented from floating from a predetermined storage position in a state in which the prefilled syringe 2 is stored.

Furthermore, when at least the part 43c of the shaft portion of the plunger 40 is stored in the proximal end side storage portion 50, the syringe body 20 of the stored prefilled syringe 2 and the plunger 40 are supported in a state in which the syringe body 20 and the plunger 40 cannot approach each other since the first contact portion 54 (here, the surface of the cutout portion 52a exposed in the distal end direction) comes into contact with the proximal end surface 21a of the body flange 21 and the second contact portion 55 (here, a part of the erected connection portion 57) comes into contact with the distal end surface 42a of the pressing operation portion 42. Therefore, the plunger 40 can be prevented from pressing the gasket 42 in a state in which the prefilled syringe 2 is stored.

Figure 19:
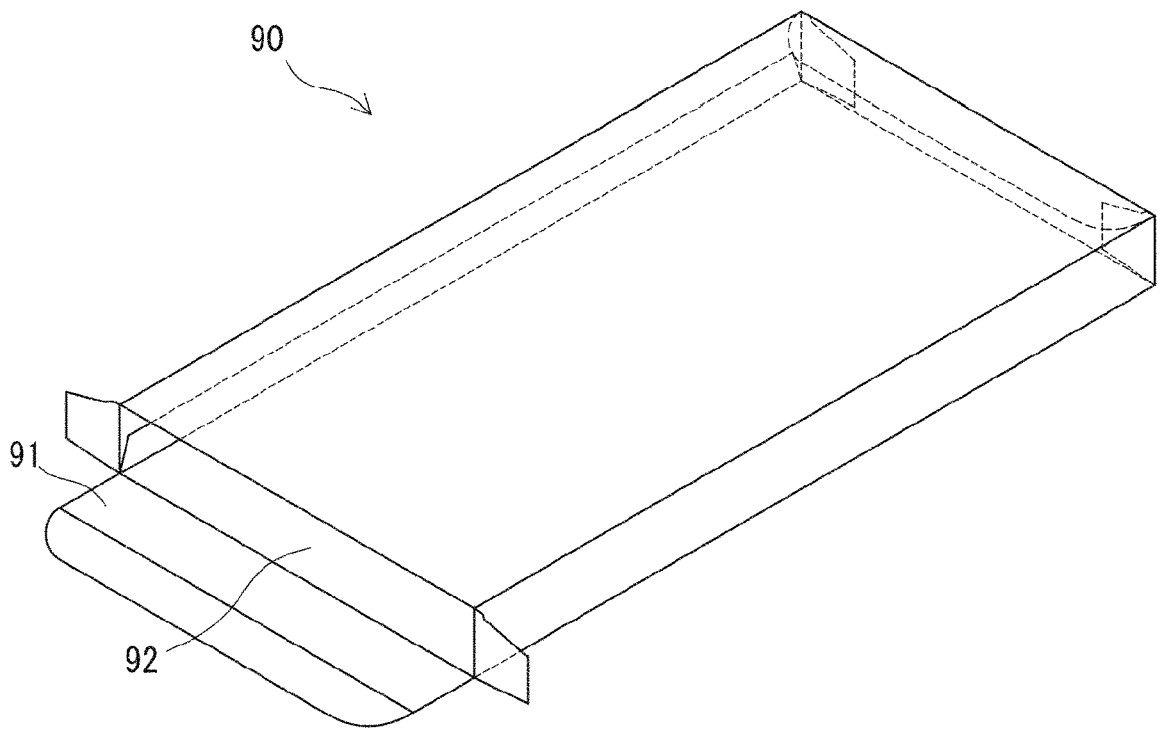
FIG. 19 is a perspective view of an outer box that stores a prefilled syringe storage tray of an example of the present disclosure.
Figure 20:
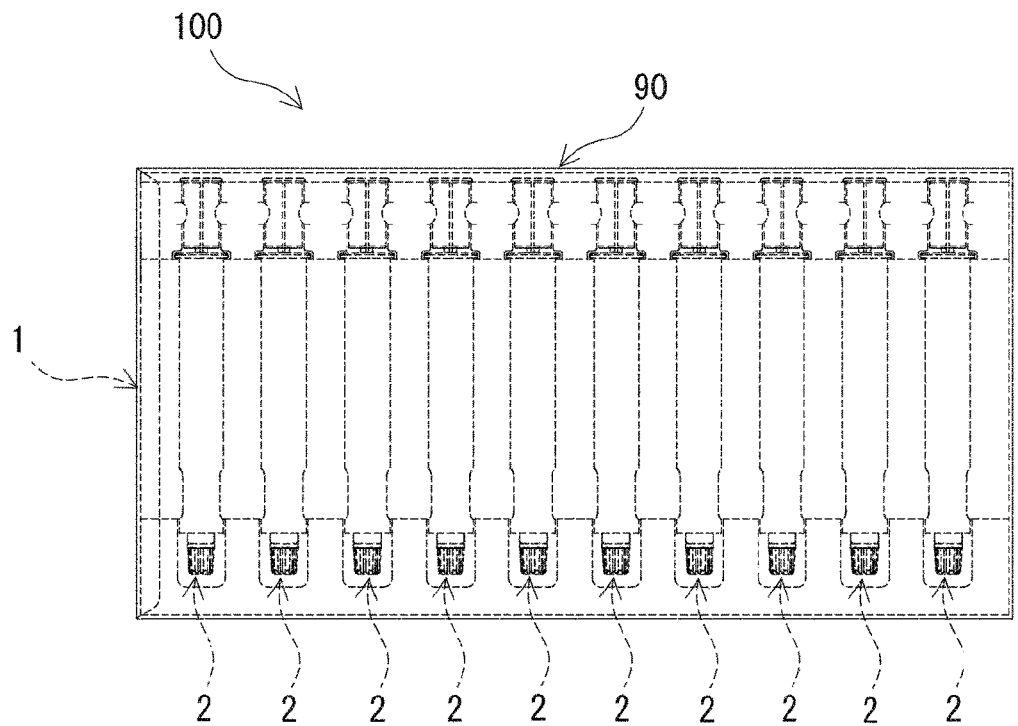
FIG. 20 is a plan view of a package of an example of the present disclosure.

The package of the present disclosure will be described with reference to FIGS. 19 and 20. In accordance with an exemplary embodiment, the package 100 of the present disclosure includes the prefilled syringe storage tray 1, the prefilled syringes 2, and the outer box 90 that stores the prefilled syringe storage tray 1 in which the prefilled syringes 2 are stored. In accordance with an exemplary embodiment, it can be preferable that the outer box 90 is made of paper and has a thin rectangular parallelepiped shape corresponding to an outer shape of the storage tray 1 as illustrated in FIG. 19, and includes an entrance 92 through which the storage tray 1 can be taken in and out and which can be closed by a lid flap 91 on at least one side surface.

The prefilled syringe storage tray of the present disclosure and the package using the same are not limited to the embodiments described above. For example, the body flange 21 may uniformly protrude from the proximal end of the syringe body 20 over the entire circumference. The syringe body 20 may have a single cylindrical structure over the entire length. A portion engaged with the engagement protrusions 75 of the storage tray 1 at the distal end portion of the syringe body 20 may be a recess that does not penetrate the outer circumferential surface of the syringe body 20 (outer cylinder 24) instead of a through hole shape like the windows 26. The shaft portion 43 of the plunger 40 may have substantially the same diameter over the entire length. In the shaft portion 43, the entire part 43c of the shaft portion disposed on the proximal end side of the syringe body 20 in the stored state may be the large diameter portion 43a.

The prefilled syringe storage tray of the present disclosure is as follows.

(1) A prefilled syringe storage tray that stores a prefilled syringe including: a syringe body including a body flange protruding outward at a proximal end portion; a sealing member sealing a distal end opening portion of the syringe body; a gasket slidably stored in the syringe body; a medicine stored in the syringe body; and a plunger for moving the gasket, which includes a gasket pressing portion provided at a distal end, a pressing operation portion provided at a proximal end, and a shaft portion connecting the gasket pressing portion with the pressing operation portion, the prefilled syringe being formed by disposing a part of the shaft portion of the plunger and the pressing operation portion on a proximal end side with respect to the syringe body, and the prefilled syringe storage tray including a base portion and a proximal end side storage portion that stands upright from the base portion and stores at least the part of the shaft portion of the plunger.

The proximal end side storage portion includes a shaft portion insertion port for inserting the part of the shaft portion of the plunger, and a pair of insertion port forming portions which are disposed to face a portion which is a side upper portion of the part of the shaft portion of the plunger stored in the proximal end side storage portion and define facing inner edges of the shaft portion insertion port.

The proximal end side storage portion includes a protruding piece extending from the inner edge of each of the insertion port forming portions toward the inner edge of the other insertion port forming portion, a first contact portion which is disposed at a first end of the shaft portion insertion port in an axial direction and with which a proximal end surface of the body flange is capable of coming into contact, and a second contact portion which is disposed at a second end facing the first end of the shaft portion insertion port in the axial direction and with which a distal end surface of the pressing operation portion is capable of coming into contact.

A distance between the facing inner edges of a pair of the insertion port forming portions is greater than a width of the part of the shaft portion of the plunger, and a distance between the facing inner edges of the insertion port forming portions in a forming portion of the protruding piece is smaller than a width of the part of the shaft portion of the plunger, and when at least the part of the shaft portion of the plunger is stored in the proximal end side storage portion, the proximal end side storage portion supports the syringe body and the plunger in a state in which the syringe body and the plunger cannot approach each other since the first contact portion comes into contact with the proximal end surface of the body flange and the second contact portion comes into contact with the distal end surface of the pressing operation portion, and the part of the shaft portion of the plunger is prevented from separating from the proximal end side storage portion since the protruding piece comes into contact with the part of the shaft portion of the plunger.

The prefilled syringe storage tray of the present disclosure includes the proximal end side storage portion storing at least the part of the shaft portion of the plunger, and the proximal end side storage portion includes the shaft portion insertion port for inserting the part of the shaft portion of the plunger, and a pair of the insertion port forming portions which are disposed to face a portion which is the side upper portion of the part of the shaft portion of the stored plunger and define the facing inner edges of the shaft portion insertion port. The proximal end side storage portion includes the protruding piece extending from the inner edge of each of the insertion port forming portions toward the inner edge of the other insertion port forming portion, the distance between the facing inner edges of a pair of the insertion port forming portions is greater than the width of the part of the shaft portion of the stored plunger, and the distance between the facing inner edges of the insertion port forming portions in the forming portion of the protruding piece is smaller than the width of the part of the shaft portion of the stored plunger. When at least the part of the shaft portion of the plunger is stored in the proximal end side storage portion, the part of the shaft portion of the plunger is prevented from separating from the proximal end side storage portion since the protruding piece comes into contact with the part of the shaft portion of the plunger. Therefore, the plunger is prevented from floating from a predetermined storage position in a state in which the prefilled syringe is stored.

Furthermore, the prefilled syringe storage tray of the present disclosure includes the proximal end side storage portion storing at least the part of the shaft portion of the plunger, and the proximal end side storage portion includes the shaft portion insertion port for inserting the part of the shaft portion of the plunger, and a pair of the insertion port forming portions which are disposed to face a portion which is the side upper portion of the part of the shaft portion of the stored plunger and define the facing inner edges of the shaft portion insertion port. The proximal end side storage portion includes the first contact portion which is disposed at the first end of the shaft portion insertion port in the axial direction and with which the proximal end surface of the body flange is capable of coming into contact, and the second contact portion which is disposed at the second end facing the first end of the shaft portion insertion port in the axial direction and with which the distal end surface of the pressing operation portion is capable of coming into contact. When at least the part of the shaft portion of the plunger is stored in the proximal end side storage portion, the syringe body of the stored prefilled syringe and the plunger are supported in a state in which the syringe body and the plunger cannot approach each other since the first contact portion comes into contact with the proximal end surface of the body flange and the second contact portion comes into contact with the distal end surface of the pressing operation portion. Therefore, the plunger can be prevented from pressing the gasket in a state in which the prefilled syringe is stored.

Furthermore, the embodiment described above may be as follows.

(2) The prefilled syringe storage tray according to (1), in which a pair of the insertion port forming portions have notches continuous with an outer edge of the protruding piece and extending in a direction opposite to the protruding piece.

(3) The prefilled syringe storage tray according to (1) or (2), in which a pair of the insertion port forming portions are plate-like portions extending substantially in parallel with the base portion.

(4) The prefilled syringe storage tray according to any one of (1) to (3), in which the proximal end side storage portion includes an erected connection portion erected from the base portion, and the erected connection portion includes the second contact portion and connects end portions of a pair of the insertion port forming portions with the base portion.

(5) The prefilled syringe storage tray according to (4), in which the erected connection portion includes a shaft portion contact portion that supports the shaft portion.

(6) The prefilled syringe storage tray according to (4) or (5), in which the erected connection portion connects the end portions of a pair of the insertion port forming portions on the second end side.

(7) The prefilled syringe storage tray according to any one of (1) to (6), in which the proximal end side storage portion includes a body flange storage portion which is adjacent to a pair of the insertion port forming portions and stores the body flange, and the body flange storage portion includes a flange insertion port that communicates with the shaft portion insertion port and is for inserting the body flange, a proximal end side support portion that is erected from the base portion and supports a portion in a vicinity of the body flange of the syringe body, and two extending portions that extend from end portions of a pair of the insertion port forming portions on the first end side to an erected end on a side opposite to the base portion of the proximal end side support portion and define inner edges of both side portions of the flange insertion port.

(8) The prefilled syringe storage tray according to (7), in which the proximal end side support portion of the body flange storage portion includes: a substantially U-shaped proximal end side cutout portion which connects the two extending portions to each other, is opened toward the erected end of the proximal end side support portion, and into which the portion in the vicinity of the body flange of the syringe body is capable of being inserted; a proximal end side contact portion formed by a portion defining an inner edge of the proximal end side cutout portion; and a movement restriction portion provided at a portion connecting the proximal end side contact portion with the base portion, and when the portion in the vicinity of the body flange of the syringe body is inserted into the proximal end side cutout portion, the proximal end side contact portion comes into contact with the portion in the vicinity of the body flange of the syringe body, and the movement restriction portion comes into contact with a distal end surface of the body flange to restrict the movement of the syringe body in the distal end direction.

(9) The prefilled syringe storage tray according to (8), in which the proximal end side contact portion includes a narrowed portion in which a width of the proximal end side cutout portion is narrower than a diameter of the syringe body, and when the portion in the vicinity of the body flange of the syringe body is inserted into the proximal end side cutout portion, the narrowed portion is engaged with the portion in the vicinity of the body flange of the syringe body to restrict removal of the portion in the vicinity of the body flange of the syringe body from the proximal end side cutout portion.

(10) The prefilled syringe storage tray according to any one of (1) to (9), further including a distal end side support portion that is erected from the base portion and supports a distal end portion of the syringe body.

(11) The prefilled syringe storage tray according to (10), in which the distal end side support portion is opened toward an erected end on a side opposite to the base portion of the distal end side support portion, and includes a substantially U-shaped distal end side cutout portion to which the distal end portion of the syringe body is capable of being inserted, the distal end side cutout portion includes a bottom portion defining a distal end side contact portion and a pair of side portions facing each other, a pair of the side portions include engagement protrusions protruding in a direction in which a pair of the side portions approach each other, and when the distal end portion of the syringe body is inserted into the distal end side cutout portion, by bringing the distal end side contact portion into contact with the distal end portion of the syringe body, the distal end side support portion supports the distal end portion of the syringe body, the engagement protrusions are engaged with the distal end portion of the syringe body, and removal of the syringe body from the distal end side cutout portion is restricted.

(12) The prefilled syringe storage tray according to (10) or (11), further including a distal end side storage portion that is adjacent to the distal end side support portion and stores at least the sealing member.

(13) The prefilled syringe storage tray according to any one of (1) to (12), in which the syringe body includes a barrel that slidably stores the gasket, stores a medicine in the barrel, and has the distal end opening portion sealed by the sealing member, and an outer cylinder that stores the barrel and is attached to the barrel.

(14) The prefilled syringe storage tray according to any one of (1) to (13), in which the proximal end side storage portion stores at least the part of the shaft portion of the plunger in a state in which the gasket pressing portion of the plunger is not in contact with the gasket.

(15) The prefilled syringe storage tray according to any one of (1) to (14), in which a plurality of the proximal end side storage portions are provided, and a plurality of the prefilled syringes are capable of being stored.

The package of the present disclosure is as follows.

(16) A package including the prefilled syringe storage tray according to any one of (1) to (15), the prefilled syringe, and an outer box that stores the prefilled syringe storage tray in which the prefilled syringe is stored.

The package of the present disclosure includes the prefilled syringe storage tray, the prefilled syringe, and the outer box that stores the prefilled syringe storage tray in which the prefilled syringe is stored. Therefore, the plunger can be prevented from pressing the gasket and from floating from a predetermined storage position simultaneously in a state in which the prefilled syringes are stored.

The detailed description above describes embodiments of a prefilled syringe storage tray and a package using the same. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A prefilled syringe storage tray configured to store a prefilled syringe, the prefilled syringe including: a syringe body including a body flange protruding outward at a proximal end portion, a sealing member sealing a distal end opening portion of the syringe body, a gasket slidably stored in the syringe body, a medicine stored in the syringe body, and a plunger for moving the gasket, which includes a gasket pressing portion provided at a distal end, a pressing operation portion provided at a proximal end, and a shaft portion connecting the gasket pressing portion with the pressing operation portion, the prefilled syringe being formed of disposing a part of the shaft portion of the plunger and the pressing operation portion on a proximal end side with respect to the syringe body, the prefilled syringe storage tray comprising:

a base portion and a proximal end side storage portion that stands upright from the base portion and stores at least the part of the shaft portion of the plunger;

wherein the proximal end side storage portion includes a shaft portion insertion port for inserting the part of the shaft portion of the plunger, and a pair of insertion port forming portions which are disposed to face a portion which is a side upper portion of the part of the shaft portion of the plunger stored in the proximal end side storage portion and define facing inner edges of the shaft portion insertion port;

the proximal end side storage portion further includes a protruding piece extending from the inner edge of each of the insertion port forming portions toward the inner edge of the other insertion port forming portion, a first contact portion which is disposed at a first end of the shaft portion insertion port in an axial direction and with which a proximal end surface of the body flange is capable of coming into contact, and a second contact portion which is disposed at a second end facing the first end of the shaft portion insertion port in the axial direction and with which a distal end surface of the pressing operation portion is capable of coming into contact;

a distance between the facing inner edges of a pair of the insertion port forming portions is greater than a width of the part of the shaft portion of the plunger, and a distance between the facing inner edges of the insertion port forming portions in a forming portion of the protruding piece is smaller than a width of the part of the shaft portion of the plunger; and when at least the part of the shaft portion of the plunger is stored in the proximal end side storage portion, the proximal end side storage portion supports the syringe body and the plunger in a state in which the syringe body and the plunger cannot approach each other since the first contact portion comes into contact with the proximal end surface of the body flange and the second contact portion comes into contact with the distal end surface of the pressing operation portion, and the part of the shaft portion of the plunger is prevented from separating from the proximal end side storage portion since the protruding piece comes into contact with the part of the shaft portion of the plunger.

2. The prefilled syringe storage tray according to claim 1, further comprising:
a pair of the insertion port forming portions have notches continuous with an outer edge of the protruding piece and extending in a direction opposite to the protruding piece.

3. The prefilled syringe storage tray according to claim 1, further comprising:
a pair of the insertion port forming portions, the pair of the insertion port forming portions being plate-like portions extending substantially in parallel with the base portion.

4. The prefilled syringe storage tray according to claim 1, wherein the proximal end side storage portion includes an erected connection portion erected from the base portion, and the erected connection portion includes the second contact portion and connects end portions of a pair of the insertion port forming portions with the base portion.

5. The prefilled syringe storage tray according to claim 4, wherein the erected connection portion includes a shaft portion contact portion that supports the shaft portion.

6. The prefilled syringe storage tray according to claim 4, wherein the erected connection portion connects the end portions of a pair of the insertion port forming portions on the second end side.

7. The prefilled syringe storage tray according to claim 1, wherein
the proximal end side storage portion includes a body flange storage portion which is adjacent to a pair of the insertion port forming portions and stores the body flange; and
the body flange storage portion includes a flange insertion port that communicates with the shaft portion insertion port and is for inserting the body flange, a proximal end side support portion that is erected from the base portion and supports a portion in a vicinity of the body flange of the syringe body, and two extending portions that extend from end portions of a pair of the insertion port forming portions on the first end side to an erected end on a side opposite to the base portion of the proximal end side support portion and define inner edges of both side portions of the flange insertion port.

8. The prefilled syringe storage tray according to claim 7, wherein
the proximal end side support portion of the body flange storage portion includes a substantially U-shaped proximal end side cutout portion which connects the two extending portions to each other, is opened toward the erected end of the proximal end side support portion, and into which the portion in the vicinity of the body flange of the syringe body is capable of being inserted, a proximal end side contact portion formed by a portion defining an inner edge of the proximal end side cutout portion, and a movement restriction portion provided at a portion connecting the proximal end side contact portion with the base portion; and
when the portion in the vicinity of the body flange of the syringe body is inserted into the proximal end side cutout portion, the proximal end side contact portion comes into contact with the portion in the vicinity of the body flange of the syringe body, and the movement restriction portion comes into contact with a distal end surface of the body flange to restrict the movement of the syringe body in a distal end direction.

9. The prefilled syringe storage tray according to claim 8, wherein the proximal end side contact portion includes a narrowed portion in which a width of the proximal end side cutout portion is narrower than a diameter of the syringe body, and when the portion in the vicinity of the body flange of the syringe body is inserted into the proximal end side cutout portion, the narrowed portion is engaged with the portion in the vicinity of the body flange of the syringe body to restrict removal of the portion in the vicinity of the body flange of the syringe body from the proximal end side cutout portion.

10. The prefilled syringe storage tray according to claim 1, further comprising:
a distal end side support portion that is erected from the base portion and supports a distal end portion of the syringe body.

11. The prefilled syringe storage tray according to claim 10, wherein the distal end side support portion is opened toward an erected end on a side opposite to the base portion of the distal end side support portion, and includes a substantially U-shaped distal end side cutout portion to which the distal end portion of the syringe body is capable of being inserted, the distal end side cutout portion includes a bottom portion defining a distal end side contact portion and a pair of side portions facing each other, a pair of the side portions include engagement protrusions protruding in a direction in which a pair of the side portions approach each other, and when the distal end portion of the syringe body is inserted into the distal end side cutout portion, by bringing the distal end side contact portion into contact with the distal end portion of the syringe body, the distal end side support portion supports the distal end portion of the syringe body, the engagement protrusions are engaged with the distal end portion of the syringe body, and removal of the syringe body from the distal end side cutout portion is restricted.

12. The prefilled syringe storage tray according to claim 10, further comprising:
a distal end side storage portion that is adjacent to the distal end side support portion and stores at least the sealing member.

13. The prefilled syringe storage tray according to claim 1, wherein the syringe body includes a barrel that slidably stores the gasket, stores a medicine in the barrel, and has the distal end opening portion sealed by the sealing member, and an outer cylinder that stores the barrel and is attached to the barrel.

14. The prefilled syringe storage tray according to claim 1, wherein the proximal end side storage portion stores at least the part of the shaft portion of the plunger in a state in which the gasket pressing portion of the plunger is not in contact with the gasket.

15. The prefilled syringe storage tray according to claim 1, comprising:
a plurality of the proximal end side storage portions, each of the plurality of the proximal end side storage portions configured to store the prefilled syringe of a plurality of prefilled syringes.

16. A prefilled syringe storage tray configured to store a plurality of prefilled syringes, each of the plurality of prefilled syringes comprises a syringe body including a body flange protruding outward at a proximal end portion, a sealing member sealing a distal end opening portion of the syringe body, a gasket slidably stored in the syringe body, a medicine stored in the syringe body, and a plunger for moving the gasket, which includes a gasket pressing portion provided at a distal end, a pressing operation portion provided at a proximal end, and a shaft portion connecting the gasket pressing portion with the pressing operation portion, the prefilled syringe being formed of disposing a part of the shaft portion of the plunger and the pressing operation portion on a proximal end side with respect to the syringe body, the prefilled syringe storage tray comprising:
  a base portion and a plurality of proximal end side storage portion that stands upright from the base portion, each of the plurality of proximal end side storage portions configured to store at least the part of the shaft portion of the plunger of one prefilled syringe of the plurality of prefilled syringes;
  the each of the plurality of proximal end side storage portions includes a shaft portion insertion port for inserting the part of the shaft portion of the plunger, and a pair of insertion port forming portions which are disposed to face a portion which is a side upper portion of the part of the shaft portion of the plunger stored in the proximal end side storage portion and define facing inner edges of the shaft portion insertion port;
  the each of the plurality of proximal end side storage portions further includes a protruding piece extending from the inner edge of each of the insertion port forming portions toward the inner edge of the other insertion port forming portion, a first contact portion which is disposed at a first end of the shaft portion insertion port in an axial direction and with which a proximal end surface of the body flange is capable of coming into contact, and a second contact portion which is disposed at a second end facing the first end of the shaft portion insertion port in the axial direction and with which a distal end surface of the pressing operation portion is capable of coming into contact;
  a distance between the facing inner edges of a pair of the insertion port forming portions is greater than a width of the part of the shaft portion of the plunger, and a distance between the facing inner edges of the insertion port forming portions in a forming portion of the protruding piece is smaller than a width of the part of the shaft portion of the plunger; and
  when at least the part of the shaft portion of the plunger is stored in the proximal end side storage portion, the proximal end side storage portion supports the syringe body and the plunger in a state in which the syringe body and the plunger cannot approach each other since the first contact portion comes into contact with the proximal end surface of the body flange and the second contact portion comes into contact with the distal end surface of the pressing operation portion, and the part of the shaft portion of the plunger is prevented from separating from the proximal end side storage portion since the protruding piece comes into contact with the part of the shaft portion of the plunger.

17. The prefilled syringe storage tray according to claim 16, wherein the each of the plurality of proximal end side storage portions include of a pair of the insertion port forming portions have notches continuous with an outer edge of the protruding piece and extending in a direction opposite to the protruding piece, and wherein the pair of the insertion port forming portions are plate-like portions extending substantially in parallel with the base portion.

18. The prefilled syringe storage tray according to claim 16, wherein the each of the plurality of proximal end side storage portions includes an erected connection portion erected from the base portion, and the erected connection portion includes the second contact portion and connects end portions of a pair of the insertion port forming portions with the base portion.

19. The prefilled syringe storage tray according to claim 16, further comprising:
  a plurality of distal end side support portions, the plurality of distal end side support portions being erected from the base portion, each of the plurality of distal end side support portion configured to support a distal end portion of the syringe body of the one prefilled syringe of the plurality of prefilled syringes; and
  wherein each of the plurality of distal end side support portions is opened toward an erected end on a side opposite to the base portion of the distal end side support portion, and includes a substantially U-shaped distal end side cutout portion to which the distal end portion of the syringe body is capable of being inserted, the distal end side cutout portion includes a bottom portion defining a distal end side contact portion and a pair of side portions facing each other, a pair of the side portions include engagement protrusions protruding in a direction in which a pair of the side portions approach each other, and when the distal end portion of the syringe body is inserted into the distal end side cutout portion, by bringing the distal end side contact portion into contact with the distal end portion of the syringe body, the distal end side support portion supports the distal end portion of the syringe body, the engagement protrusions are engaged with the distal end portion of the syringe body, and removal of the syringe body from the distal end side cutout portion is restricted.

20. A package comprising:
  a prefilled syringe, the prefilled syringe comprising:
    a syringe body including a body flange protruding outward at a proximal end portion, a sealing member sealing a distal end opening portion of the syringe body, a gasket slidably stored in the syringe body, a medicine stored in the syringe body, and a plunger for moving the gasket, which includes a gasket pressing portion provided at a distal end, a pressing operation portion provided at a proximal end, and a shaft portion connecting the gasket pressing portion with the pressing operation portion, the prefilled syringe being formed of disposing a part of the shaft portion of the plunger and the pressing operation portion on a proximal end side with respect to the syringe body;
  a prefilled syringe storage tray comprising:
    a base portion and a proximal end side storage portion that stands upright from the base portion and stores at least the part of the shaft portion of the plunger;
    wherein the proximal end side storage portion includes a shaft portion insertion port for inserting the part of the shaft portion of the plunger, and a pair of insertion port forming portions which are disposed to face a portion which is a side upper portion of the part of the shaft portion of the plunger stored in the proximal end side storage portion and define facing inner edges of the shaft portion insertion port;
    the proximal end side storage portion includes a protruding piece extending from the inner edge of each of the insertion port forming portions toward the inner edge of the other insertion port forming portion, a first contact portion which is disposed at a first end of the shaft portion insertion port in an axial direction and with which a proximal end surface of the body flange is capable of coming into contact, and a second contact portion which is disposed at a second end facing the first end of the shaft portion insertion port in the axial direction and with which a distal end surface of the pressing operation portion is capable of coming into contact;

a distance between the facing inner edges of a pair of the insertion port forming portions is greater than a width of the part of the shaft portion of the plunger, and a distance between the facing inner edges of the insertion port forming portions in a forming portion of the protruding piece is smaller than a width of the part of the shaft portion of the plunger; and when at least the part of the shaft portion of the plunger is stored in the proximal end side storage portion, the proximal end side storage portion supports the syringe body and the plunger in a state in which the syringe body and the plunger cannot approach each other since the first contact portion comes into contact with the proximal end surface of the body flange and the second contact portion comes into contact with the distal end surface of the pressing operation portion, and the part of the shaft portion of the plunger is prevented from separating from the proximal end side storage portion since the protruding piece comes into contact with the part of the shaft portion of the plunger; and an outer box that stores the prefilled syringe storage tray in which the prefilled syringe is stored.

* * * * *